US00PP26030P3

(12) United States Plant Patent
Olesen

(10) Patent No.: US PP26,030 P3
(45) Date of Patent: Nov. 3, 2015

(54) GROUND COVER ROSE PLANT NAMED 'POULTC017'

(50) Latin Name: ***Rosa* hybrid**
Varietal Denomination: Poultc017

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 168 days.

(21) Appl. No.: 13/986,939

(22) Filed: Jun. 14, 2013

(65) Prior Publication Data

US 2014/0373226 P1 Dec. 18, 2014

(51) Int. Cl.
*A01H 5/02* (2006.01)

(52) U.S. Cl.
USPC ..... Plt./125

(58) Field of Classification Search
USPC ..... Plt./104, 125, 145
CPC ..... A01H 5/0222; A01H 5/02; A01H 5/0216; A01H 5/00
See application file for complete search history.

(56) References Cited

PUBLICATIONS

Poulsen Roser A/S, Excellent Cover, retrieved on Jan. 14, 2015, retrieved from the Internet at <www.poulsenroser.com/assortment/rose-collections/towne-country/excellent-cover.aspx> one page.*
Upov Pluto Plant Variety Database 20150114 for *Rosa* 'Poultc017', retrieved on Jan. 14, 2015, retrieved from the Internet <www3.wipo.int/pluto/user/en/index.jsp> one page.*

* cited by examiner

*Primary Examiner* — June Hwu

(57) ABSTRACT

A new garden rose plant of the Ground Cover class which has abundant, yellow flowers and attractive foliage. This new and distinct variety has shown to be uniform and stable in the resulting generations from asexual propagation.

2 Drawing Sheets

Botanical designation: *Rosa* hybrid.
Variety denomination: 'Poultc017'.

SUMMARY OF THE INVENTION

The present invention constitutes a new and distinct variety of garden rose plant which originated from a controlled crossing between the female seed parent, an unnamed seedling, and the male pollen parent, also an unnamed seedling.

The two parents were crossed during the summer of 2005 and the resulting seeds were planted in a controlled environment in Fredensborg, Denmark. The new variety, named 'Poultc017', originated as a single seedling from the stated cross.

The new variety may be distinguished from its male pollen parent and female seed parent primarily by flower coloration and growth habit.

The objective of the hybridization of this rose variety was to create a new and distinct variety for garden use with unique qualities, such as:

1. Uniform and abundant yellow flowers;
2. Vigorous, but compact growth when propagated both as a budded rose and on its own roots; and
3. Exceptional disease resistance.

This combination of qualities is not present in previously available commercial cultivars of this type, known to the inventor, and distinguish 'Poultc017' from all other varieties of which we are aware.

As part of the rose development program, Mogens N. Olesen germinated the seeds from the aforementioned hybridization during winter of 2005 and conducted evaluations on the resulting seedlings in a controlled environment in Fredensborg, Denmark. 'Poultc017' was selected in the spring of 2006 by the inventor as a single plant from the progeny of the aforementioned hybridization.

Asexual reproduction of 'Poultc017' by traditional budding and rooted cuttings was first done by Mogens N. Olesen in the nursery in Fredensborg, Denmark in July, 2006. This initial and other subsequent asexual propagations conducted in controlled environments have demonstrated that the characteristics of 'Poultc017' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poultc017'.

Specifically illustrated in FIG. 1 are flowers at various stages of development, flower in parts, leaves, and stems.

DETAILED DESCRIPTION OF THE VARIETY

Figure 1:
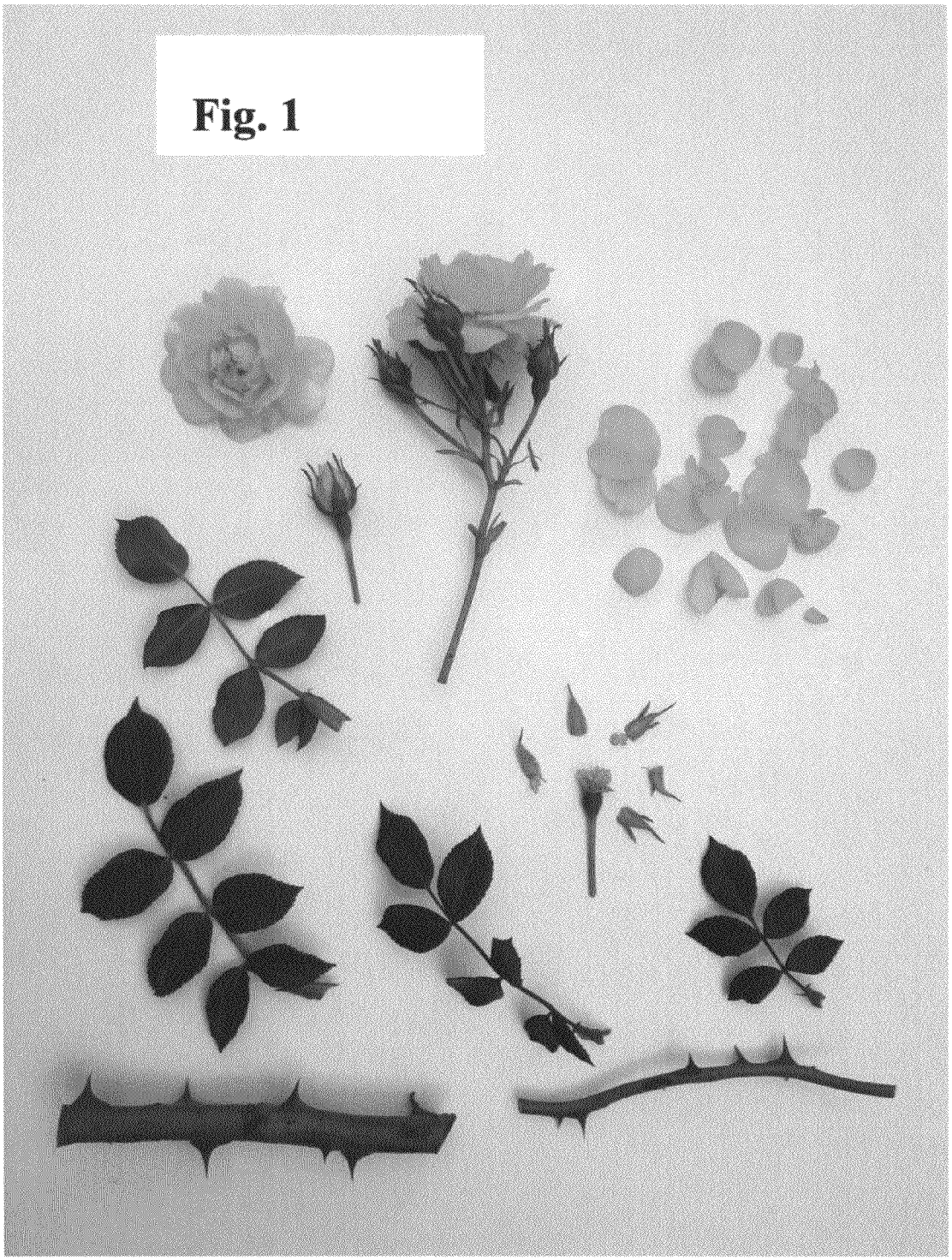
Figure 2:
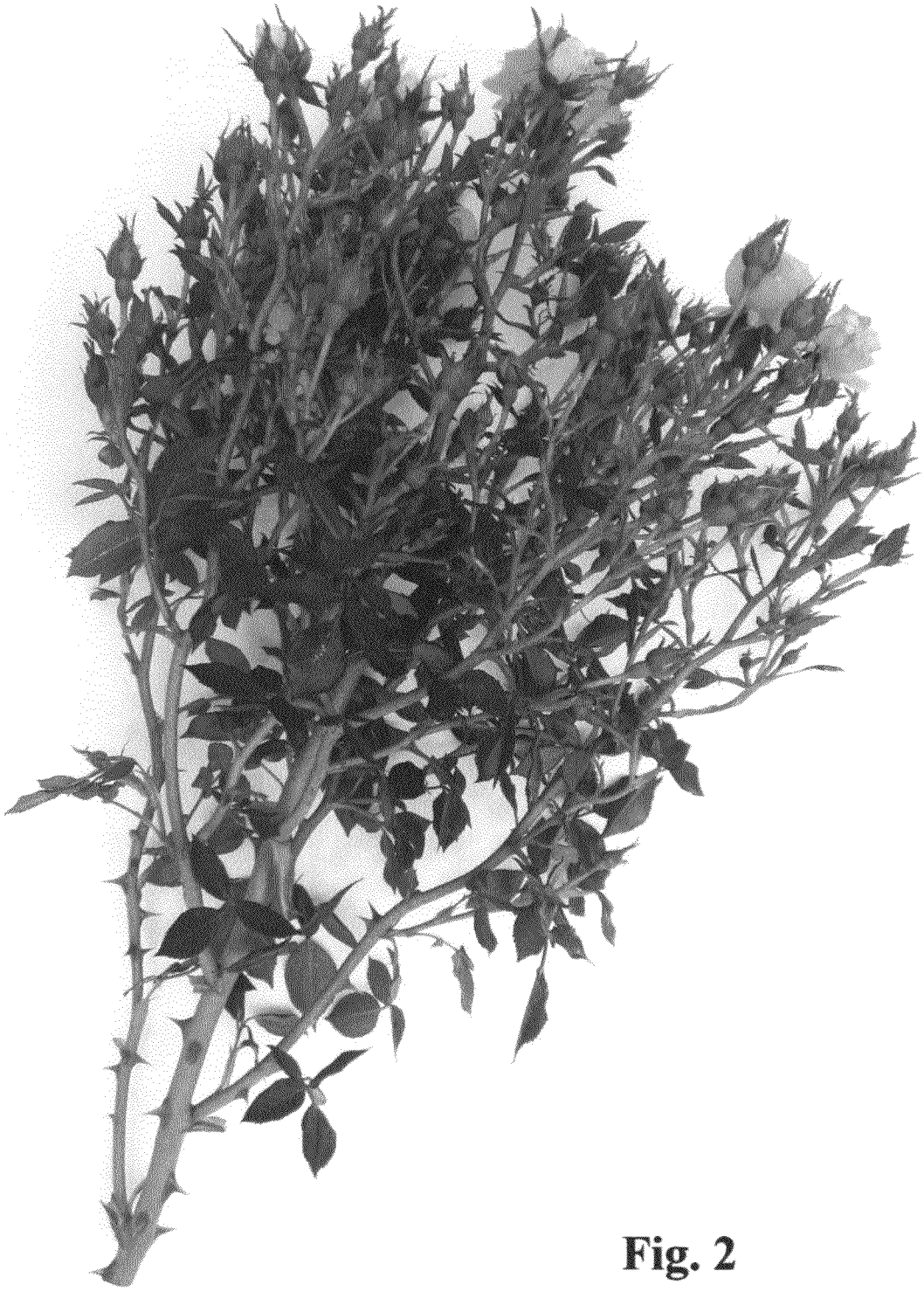
FIG. 2 is a flowering branch, showing arrangement of flower buds and peduncles.

The following is a description of 'Poultc017', as observed in its growth in in a field nursery in Benton County Oreg.. Observed plants are 1 year of age, and were grown on their own roots. Color references are made using The Royal Horticultural Society (London, England) Colour Chart, 2001, except where common terms of color are used.

For a comparison, several physical characteristics of the rose variety 'Poultc014', U.S. Plant Pat. No. 18,444 are compared to 'Poultc017' in Chart 1.

CHART 1

| | 'Poultc017' | 'Poultc014' |
|---|---|---|
| Petal Count | 28 | 35 |
| Flower Diameter | 50 mm | 30 mm |
| General Tonality of Flower Color | Combination of Yellow Group 9B and Yellow-Orange Group 15B. | Yellow Group 8A to Yellow Group 10B |

Flower and Flower Bud

Blooming habit: Continuous.

Flower bud:

*Size*.—Upon opening, 25 mm in length from base of receptacle to end of bud. Bud diameter is 10 mm.

*Bud form*.—Ovate.

*Bud color*.—As sepals divide, petals are Yellow Group 13B and 13A. Apex of the sepals is colored Greyed-Purple183A.

*Sepal inner surface*.—Color: Yellow-Green Group 147C. Surface: Smooth and pubescent.

*Sepal outer surface*.—Color: Yellow-Green Group 146B. Texture: Rough.

*Sepal shape*.—Apex: Cirrhose. Base: Flat at union with receptacle.

*Sepal margin*.—Margins have moderate foliaceous appendages on three of the five sepals.

*Sepal size*.—23 mm long by 6 mm wide.

*Receptacle*.—Texture: Smooth. Size: 6 mm in height by 5 mm wide. Color: Yellow-Green Group 146A. Shape: Elliptical.

*Pedicel*.—Surface: Somewhat rough with stipitate glands. Length: 23 mm. Diameter: 3 mm on average. Color: Yellow-Green Group 144C. Stipitate glands are Greyed-Red Group 180A. Strength: Strong.

*Peduncle*.—Length: 2 to 25 cm. Diameter: 2 to 4 mm. Color: Yellow-Green Group 145A.

Flower bud development: Flower buds are borne in clusters of 3 to 7 flower buds per stem, resembling a panicle.

Flower bloom:

*Fragrance*.—None.

*Duration*.—The blooms have a duration on the plant of approximately 7 to 10 days. Petals fall cleanly away from plant after flowers have fully matured.

*Size*.—Flower diameter is 50 mm when open. Flower depth is 20 mm.

*Flower shape*.—General shape is an open rosette.

*Shape of flower, side view*.—The upper portion is a flattened convex. The lower portion is concave.

Petalage: Semi-double. Under normal conditions, flowers have 28 petals total, 3 to 4 of which are petaloids.

General tonality of flower: Open flowers are a combination of Yellow Group 9B and Yellow-Orange Group 15B.

Petal color:

*Upon opening, outer petals*.—Upper surface: Yellow Group 12A with shades of Yellow Group 8B. Lower surface: Yellow Group 11A with intonations of Yellow-Orange Group 15B.

*Upon opening, inner petals*.—Upper surface: Yellow Group 12A. Lower surface: Yellow-Orange Group 14C.

*After opening, outer & inner petals*.—Upper surface: Yellow Group 12A with shades of Yellow Group 8B. Lower surface: Yellow Group 11A with intonations of Yellow-Orange Group 15B.

Petals:

*Petal reflex*.—Slightly reflexed.

*Margin*.—Entire and uniform with a small point at the center apex. Weak undulations of margin observed.

*Shape*.—Generally rounded. Apex shape: Rounded, and occasionally flat. Base shape: Acute.

*Size*.—23 mm (l)×23 mm (w).

*Texture*.—Smooth.

*Thickness*.—Average.

Reproductive organs:

*Pollen*.—None observed.

*Anthers*.—Size: 2 mm in length. Color: Yellow Group 12B. Quantity: 20 on average.

*Filaments*.—Color: Yellow-Orange Group 14A. Length: 3 mm.

*Pistils*.—Length: 3 mm. Quantity: 18 on average.

Stigmas.—Color: Yellow-Green Group 154C.

Styles.—Color: Yellow-Green Group 154C.

*Location of stigmas*.—Slightly inferior in location relative to the length of the filaments and the height of the anthers.

*Hips*.—None Observed.

Plant

Plant growth: Upright and bushy. Plants are 50 to 60 cm in height, and 40 to 60 cm wide.

Stems:

Color.—Juvenile growth: Yellow-Green Group 144B. Mature growth: Yellow-Green Group 144A.

*Length*.—On average, canes are 35 cm from the base of the plant to the flowering portion.

*Diameter*.—9 mm.

*Internodes*.—On mature canes, there is an average distance of 60 mm between nodes.

*Surface texture*.—Young wood: Smooth. Older wood: Smooth.

Long prickles:

*Incidence*.—9 prickles per 10 cm of stem.

*Size*.—Average length of prickles on mature stems is 8 mm.

*Shape*.—Upper portion is linear. Lower portion is concave.

*Color*.—Juvenile prickles: Greyed-Red Group 179A. Mature prickles: Greyed-Red Group 181A.

Plant foliage:

*Compound leaf*.—110 mm (l) 70 mm (w).

*Quantity*.—2 leaves per 10 cm of stem on average.

*Leaf bearing angle to the stem*.—45 degrees.

*Color of juvenile foliage*.—Upper side: Yellow-Green Group 147A. Lower side: Yellow-Green Group 146B.

*Color of mature foliage*.—Upper side: Yellow-Green Group 147A. Lower side: Yellow-Green Group 146B.

Plant leaves and leaflets:

*Stipules*.—Size: 15 mm in length. Quantity: 2 per compound leaf. Shape: Linear, slightly broad based with outward extending apecies. Margins: Finely serrated with few stipitate glands. Color: Yellow-Green Group 144A with Greyed-Orange Group 166B.

*Petiole*.—Length: 20 mm. Diameter: 1 mm.

*Upper surface*.—Color: Yellow-Green Group 144A.

*Lower surface*.—Color: Yellow-Green Group 144A. Observations: Smooth.

*Rachis*.—Length: 50 mm. Upper surface: Color: Yellow-Green Group 144A. On juvenile leaflets, Greyed-Purple Group 183A.

*Lower surface*.—Color: Yellow-Green Group 144A. Observations: Few small prickles observed.

*Leaflet*.—Quantity: Normal number of leaflets leaves in middle of the stem is 7 leaflets. Margins: Serrated. Size: Average size of the terminal leaflet on normal leaves is 31 mm in length by 21 mm wide. Shape: Generally elliptical. Base: Rounded. Apex: Cuspidate. Texture: Smooth. Thickness: Average. Arrangement: Odd pinnate. Venation: Reticulate. Glossiness: Glossy.

Disease resistance: Above average resistance to powdery and downy mildew, rust, black spot, and Botrytis under normal growing conditions.

Cold hardiness: The variety is tolerant to USDA Cold Hardiness Zone 6.

Heat tolerance: The variety has been found to be suitable for climate conditions found in the American Horticulture Society heat zone 7.

The invention claimed is:

1. A new and distinct variety of rose plant of the Ground Cover rose class named 'Poultc017', substantially as illustrated and described herein, due to its abundant yellow flowers, disease resistance, and extended period of bloom.

* * * * *